United States Patent
McKay et al.

(10) Patent No.: US 7,887,593 B2
(45) Date of Patent: Feb. 15, 2011

(54) METHOD OF IMPLANTING NATURAL TISSUE WITHIN THE VERTEBRAL DISC NUCLEUS SPACE USING A DRAWSTRING

(75) Inventors: William F. McKay, Memphis, TN (US); Hai H. Trieu, Cordova, TN (US)

(73) Assignee: Warsaw Orthopedic, Inc.

( * ) Notice: Subject to any disclaimer, the term of this patent is extended or adjusted under 35 U.S.C. 154(b) by 689 days.

(21) Appl. No.: 10/666,900

(22) Filed: Sep. 18, 2003

(65) Prior Publication Data

US 2004/0059418 A1 Mar. 25, 2004

Related U.S. Application Data

(63) Continuation-in-part of application No. 10/645,006, filed on Aug. 21, 2003, now Pat. No. 7,309,359, and a continuation-in-part of application No. 10/245,955, filed on Sep. 18, 2002, now abandoned.

(60) Provisional application No. 60/411,547, filed on Sep. 18, 2002, provisional application No. 60/426,613, filed on Nov. 15, 2002.

(51) Int. Cl.
*A61F 2/44* (2006.01)
(52) U.S. Cl. .................... 623/17.16; 623/908
(58) Field of Classification Search .......... 606/61, 606/108, 151, 213, 216; 623/17.11, 17.12, 623/17.16, 902, 908, 925, 1.11, 13.17, 13.19
See application file for complete search history.

(56) References Cited

U.S. PATENT DOCUMENTS

| | | | |
|---|---|---|---|
| 3,551,560 A | 12/1970 | Thiele | |
| 3,610,243 A * | 10/1971 | Jones, Sr. | 604/375 |
| 3,855,638 A | 12/1974 | Pilliar | |
| 3,875,595 A | 4/1975 | Froning | |
| 4,060,081 A | 11/1977 | Yannas et al. | |
| 4,085,466 A | 4/1978 | Goodfellow et al. | |
| 4,280,954 A | 7/1981 | Yannas et al. | |
| 4,344,193 A | 8/1982 | Kenny | |
| 4,349,921 A | 9/1982 | Kuntz | |
| 4,350,629 A | 9/1982 | Yannas et al. | |
| 4,378,224 A | 3/1983 | Nimni et al. | |

(Continued)

FOREIGN PATENT DOCUMENTS

EP 00305026 3/1988

(Continued)

OTHER PUBLICATIONS

FASCIAN—Printout from website: fascian.com.

*Primary Examiner*—Brian E. Pellegrino

(57) ABSTRACT

Materials and methods for repairing or replacing an intervertebral disc or disc nucleus using natural biological tissue. The tissue may be used alone without an additional core material, or it may be used to encapsulate an elastomeric or hydrogel core. When used alone the tissue may be rolled, folded, braided, or layered to provide a solid plug of natural biological material. When used to encapsulate an elastomeric or hydrogel core the tissue acts as a constraining jacket to support the core. The natural tissue implants may further include a drawstring to assist in folding the implant when the device is implanted in an intervertebral disc space. Multiple units of the natural tissue implants may be used together.

9 Claims, 21 Drawing Sheets

U.S. PATENT DOCUMENTS

| | | | |
|---|---|---|---|
| 4,400,833 A | 8/1983 | Kurland | |
| 4,418,691 A | 12/1983 | Yannas et al. | |
| 4,448,718 A | 5/1984 | Yannas et al. | |
| 4,458,678 A | 7/1984 | Yannas et al. | |
| 4,505,266 A | 3/1985 | Yannas et al. | |
| 4,544,516 A | 10/1985 | Hughes et al. | |
| 4,578,079 A | 3/1986 | Ruoslahti et al. | |
| 4,585,458 A * | 4/1986 | Kurland | 623/13.17 |
| 4,589,881 A | 5/1986 | Pierschbacher et al. | |
| 4,614,794 A | 9/1986 | Easton et al. | |
| 4,627,853 A | 12/1986 | Campbell et al. | |
| 4,642,120 A | 2/1987 | Nevo et al. | |
| 4,661,111 A | 4/1987 | Ruoslahti et al. | |
| 4,772,287 A | 9/1988 | Ray et al. | |
| 4,787,900 A | 11/1988 | Yannas | |
| 4,801,299 A | 1/1989 | Brendel et al. | |
| 4,837,285 A | 6/1989 | Berg et al. | |
| 4,879,135 A | 11/1989 | Greco et al. | |
| 4,880,492 A | 11/1989 | Erdmann et al. | |
| 4,904,260 A | 2/1990 | Ray et al. | |
| 4,946,792 A | 8/1990 | O'Leary | |
| 4,976,733 A | 12/1990 | Girardot | |
| 5,007,934 A | 4/1991 | Stone | |
| 5,067,962 A | 11/1991 | Campbell et al. | |
| 5,108,438 A | 4/1992 | Stone | |
| 5,139,069 A * | 8/1992 | Hong | 160/84.04 |
| 5,229,497 A | 7/1993 | Boni | |
| 5,258,043 A | 11/1993 | Stone | |
| 5,279,539 A * | 1/1994 | Bohan et al. | 600/37 |
| 5,507,810 A | 4/1996 | Prewett et al. | |
| 5,607,476 A | 3/1997 | Prewett et al. | |
| 5,713,959 A | 2/1998 | Bartlett et al. | |
| 5,733,337 A | 3/1998 | Carr, Jr. et al. | |
| 5,922,028 A | 7/1999 | Plouhar et al. | |
| 5,964,807 A | 10/1999 | Gan et al. | |
| 5,980,504 A | 11/1999 | Sharkey et al. | |
| 6,007,570 A | 12/1999 | Sharkey et al. | |
| 6,025,538 A | 2/2000 | Yaccarino, III | |
| 6,073,051 A | 6/2000 | Sharkey et al. | |
| 6,077,989 A | 6/2000 | Kandel et al. | |
| 6,080,194 A | 6/2000 | Pachence et al. | |
| 6,095,149 A | 8/2000 | Sharkey et al. | |
| 6,099,514 A | 8/2000 | Sharkey et al. | |
| 6,122,549 A | 9/2000 | Sharkey et al. | |
| 6,123,731 A | 9/2000 | Boyce et al. | |
| 6,126,682 A | 10/2000 | Sharkey et al. | |
| 6,140,452 A | 10/2000 | Felt et al. | |
| 6,146,422 A | 11/2000 | Lawson | |
| 6,176,880 B1 | 1/2001 | Plouhar et al. | |
| 6,224,630 B1 | 5/2001 | Bao et al. | |
| 6,240,926 B1 | 6/2001 | Chin Gan et al. | |
| 6,261,311 B1 | 7/2001 | Sharkey et al. | |
| 6,264,695 B1 | 7/2001 | Stoy | |
| 6,290,715 B1 | 9/2001 | Sharkey et al. | |
| 6,306,169 B1 | 10/2001 | Lee et al. | |
| 6,306,177 B1 | 10/2001 | Felt et al. | |
| 6,322,786 B1 | 11/2001 | Anderson | |
| 6,340,369 B1 | 1/2002 | Ferree | |
| 6,344,058 B1 | 2/2002 | Ferree | |
| 6,352,557 B1 | 3/2002 | Ferree | |
| 6,352,558 B1 | 3/2002 | Spector | |
| 6,402,784 B1 | 6/2002 | Wardlaw | |
| 6,425,919 B1 | 7/2002 | Lambrecht | |
| 6,428,576 B1 | 8/2002 | Haldimann | |
| 6,620,196 B1 * | 9/2003 | Trieu | 623/17.16 |
| 6,733,505 B2 * | 5/2004 | Li | 606/99 |
| 6,736,838 B1 * | 5/2004 | Richter | 623/1.11 |
| 6,936,070 B1 * | 8/2005 | Muhanna | 623/17.12 |
| 2002/0026244 A1 | 2/2002 | Trieu | |
| 2002/0038150 A1 | 3/2002 | Urry | |
| 2002/0099258 A1* | 7/2002 | Staskin et al. | 600/30 |
| 2002/0107570 A1* | 8/2002 | Sybert et al. | 623/17.11 |
| 2002/0116069 A1 | 8/2002 | Urry | |
| 2002/0120270 A1 | 8/2002 | Trieu et al. | |
| 2002/0151979 A1* | 10/2002 | Lambrecht et al. | 623/17.16 |
| 2002/0151981 A1 | 10/2002 | Ferree | |

FOREIGN PATENT DOCUMENTS

| | | |
|---|---|---|
| EP | 00277678 | 10/1988 |
| FR | 2651994 A * | 3/1991 |
| WO | WO8910728 | 11/1989 |
| WO | WO 02/017824 | 3/2002 |
| WO | WO 02/034169 | 5/2002 |
| WO | WO 02/039889 | 5/2002 |
| WO | WO 03/066120 | 8/2003 |
| WO | WO 2004/026189 | 4/2004 |

* cited by examiner

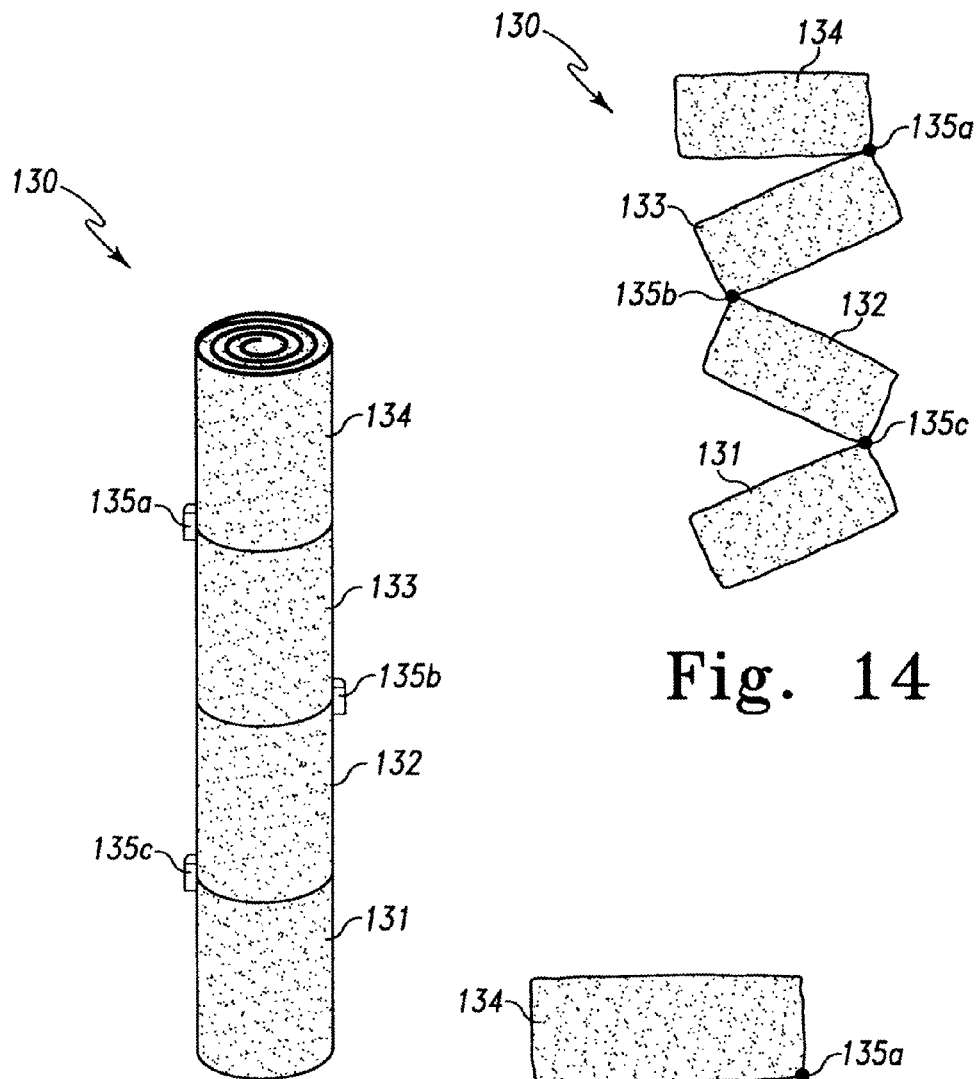
Fig. 14
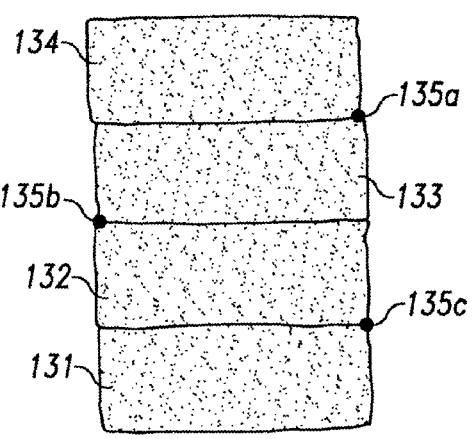
Fig. 13
Fig. 15

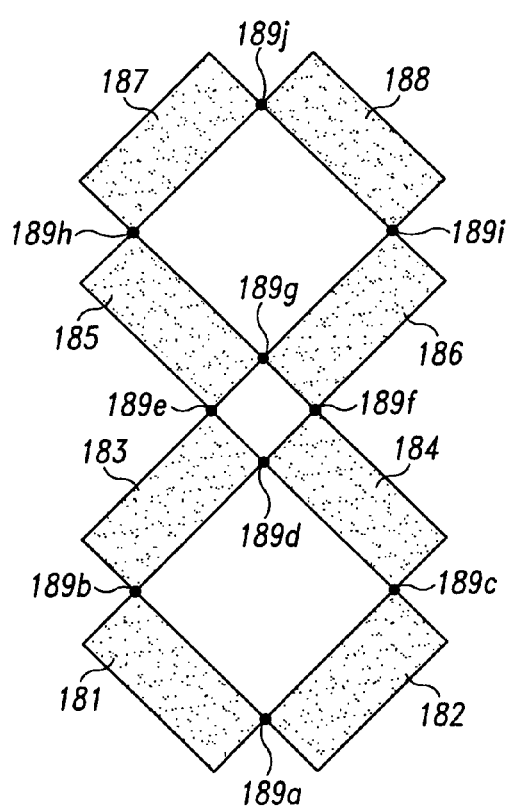
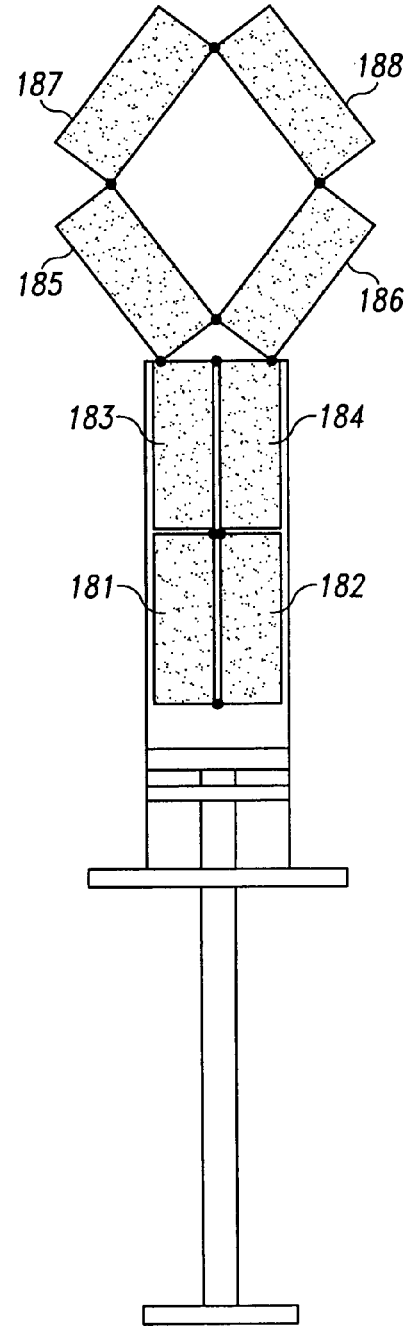
Fig. 18
Fig. 19

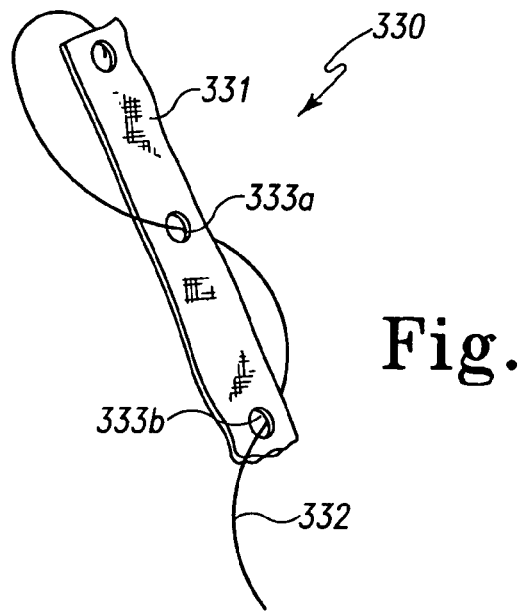
Fig. 33
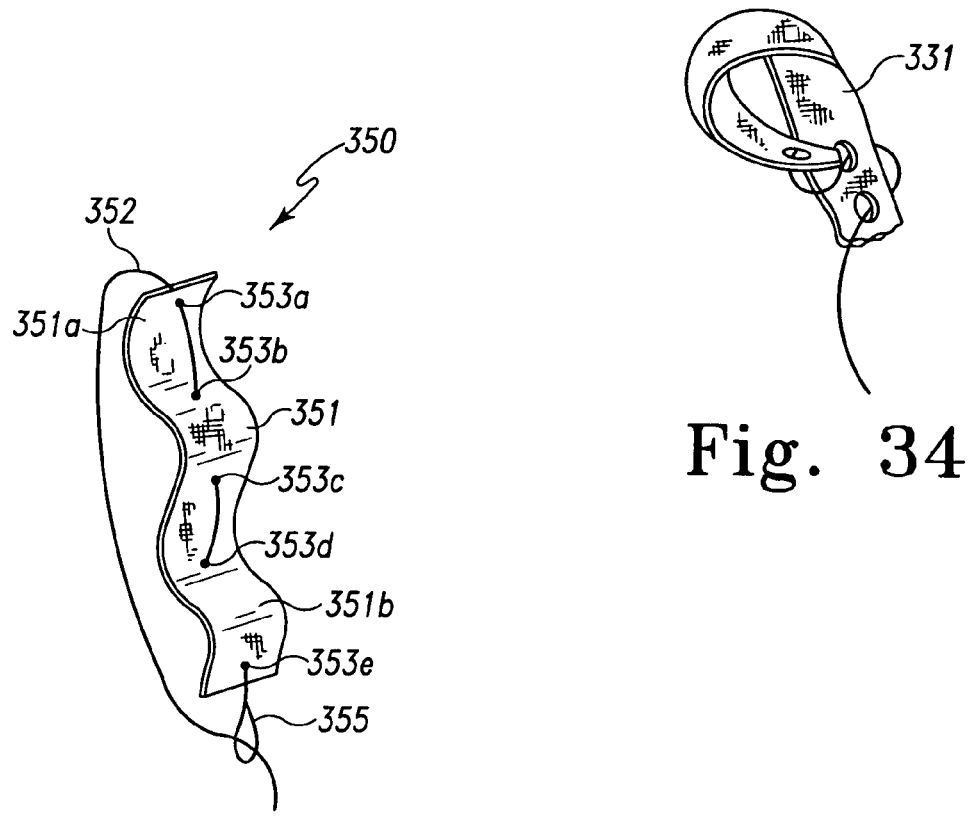
Fig. 34
Fig. 35

METHOD OF IMPLANTING NATURAL TISSUE WITHIN THE VERTEBRAL DISC NUCLEUS SPACE USING A DRAWSTRING

CROSS-REFERENCE TO RELATED APPLICATIONS

This application is a continuation-in-part of U.S. patent application Ser. No. 60/411,547, filed Sep. 18, 2002; of U.S. patent application Ser. No. 10/645,006, filed Aug. 21, 2003 now U.S. Pat. No. 7,309,359; of U.S. patent application Ser. No. 10/245,955, filed Sep. 19, 2002, now abandoned; and of U.S. patent application Ser. No. 60/426,613, filed Nov. 15, 2002. All of the foregoing are hereby incorporated by reference into this application in their entirety.

FIELD OF THE INVENTION

The present invention relates generally to the use of natural tissue to augment or repair orthopedic structures, and more particularly to the use of natural tissue to augment or repair orthopedic structures such as intervertebral discs and/or synovial joints.

BACKGROUND OF THE INVENTION

The intervertebral disc functions to stabilize the spine and to distribute forces between vertebral bodies. A normal disc includes a gelatinous nucleus pulposus, an annulus fibrosis and two vertebral end plates. The nucleus pulposus is surrounded and confined by the annulus fibrosis.

It is known that intervertebral discs are prone to injury and degeneration. For example, herniated discs are common, and typically occur when normal wear, or exceptional strain, causes a disc to rupture. Degenerative disc disease typically results from the normal aging process, in which the tissue gradually looses its natural water and elasticity, causing the degenerated disc to shrink and possibly rupture.

Intervertebral disc injuries and degeneration are frequently treated by replacing or augmenting the existing disc material. Current intervertebral disc replacement procedures tend to utilize synthetic materials such as polyethylene mesh to encapsulate a central core of hydrogel. These synthetic materials are woven into textured fabrics whose rough surfaces may accelerate wear of the encapsulated hydrogel or the bone endplates of the intervertebral body. Such wear may generate wear particles, and can cause adverse biological responses such as osteolysis in the vertebral body endplate bone and subsequent subsidence of the implant.

For example, reports on the use of prosthetic nucleus replacement devices with polyethylene mesh jackets have indicated subsidence of these devices into the endplates of the vertebral bodies. Subsidence is also due to the rigid compliance of the jacket and hard hydrogel core. This modulus mismatch with the vertebral bone, combined with the other design features mentioned above, contributes to implant subsidence.

In addition to intervertebral discs and joints, other synovial joints are present in the mammalian appendicular skeleton. A typical synovial joint comprises two bone ends covered by layer of articular cartilage. The cartilage is smooth and resilient, and facilitates low-friction movement of the bones in the joint.

The bone ends and associated cartilage are surrounded by a joint capsule—a "sack" of membrane that produces synovial fluid. The capsule and fluid protect and support the cartilage and connective tissue, carrying nutrients to the articular cartilage and removing the metabolic wastes.

The articular cartilage is a thin (2-3 mm) layer of hyaline cartilage on the epiphysis of the bone. It lacks a perichondrium, and thus has a limited capacity for repair when damaged. Additionally, the natural aging process can cause the articular cartilage to degenerate somewhat, reducing its capacity to protect and cushion the bone ends.

Zygapophysial joints, better known as facet joints, are the mechanism by which each vertebra of the spine connects to the vertebra above and/or below it. Each joint comprises two facet bones—an inferior facet and a superior facet—with the inferior facet of one vertebra connecting to the superior facet of an adjacent vertebra. The joints facilitate movement of the vertebra relative to each other, and allow the spine to bend and twist.

As in all synovial joints, where the facets contact each other there is a lining of cartilage lubricated by a thin layer of synovial fluid. The cartilage and synovial fluid decrease friction at the joint, extending joint life and preventing inflammation and associated pain.

As the natural aging process progresses, the cartilage covering the joint may deteriorate and start to fray. The fraying process may cause pieces of cartilage to break free, and the previously smooth surfaces may become rough. The facet bones then begin to rub together, creating friction which leads to further deterioration of the joint. Moreover, the nerves associated with the joint become irritated and inflamed, causing severe pain and restricting movement of the spine.

Techniques for addressing degeneration of synovial joints in general, and facet joints in particular, joint have heretofore relied primarily on injections to block pain and reduce inflammation. This treatment is only temporary though, and rarely leads to any significant improvement of the underlying condition.

It can be seen from the above that a need exists for vertebral disc implants that avoid the problems associated with the use of synthetic materials in augmenting, repairing or replacing all or part of an intervertebral disc. It can also be seen that a need exists for materials and methods effective for treating degenerating synovial joints, and particularly for materials and methods effective for supplementing or replacing the cartilage that lubricates and protects the joint. The present invention addresses those needs.

SUMMARY OF THE INVENTION

One aspect of the present invention provides materials and methods for augmenting, repairing, or replacing portions or all of an intervertebral disc using natural biological tissue. The tissue may be provided in strips, sheets, or plugs, among other forms, and each piece may be rolled, folded, braided, etc., to form a desired configuration. The tissue may be used alone, or it may be used in combination with other pieces of natural materials or with a second material.

Alternatively, the natural tissue may be used alone or with another material to augment or repair any synovial joint or other anatomical structure. Braided natural tissue segments, in particular, find utility in a variety of orthopedic applications.

Additional features and benefits of the present invention shall become apparent from the following description of the preferred embodiments.

BRIEF DESCRIPTION OF THE DRAWINGS

FIG. 13 shows a natural tissue implant made from a multiplicity of sub-units, with each sub-unit comprising a roll of tissue.

FIG. 14 shows the natural tissue implant of FIG. 13, with the sub-units being folded over to form a wider implant.

FIG. 15 shows the natural tissue implant of FIG. 13, after the sub-units have been folded over to form a wider implant.

FIG. 18 shows a natural tissue implant made from a multiplicity of sub-units in an "accordion" embodiment.

FIG. 19 shows the natural tissue implant of FIG. 18, with the sub-units being folded to form a narrower implant.

FIG. 33 shows and alternative embodiment of the present invention, with a braided tissue implant being formed into a knot.

FIG. 34 shows the implant of FIG. 33, after the braided tissue implant has been formed into a knot.

FIG. 35 shows a further embodiment of the natural tissue implants of the present invention, showing the use of a drawstring to bunch or fold an unbraided implant.

DESCRIPTION OF THE PREFERRED EMBODIMENTS

Figure 1:
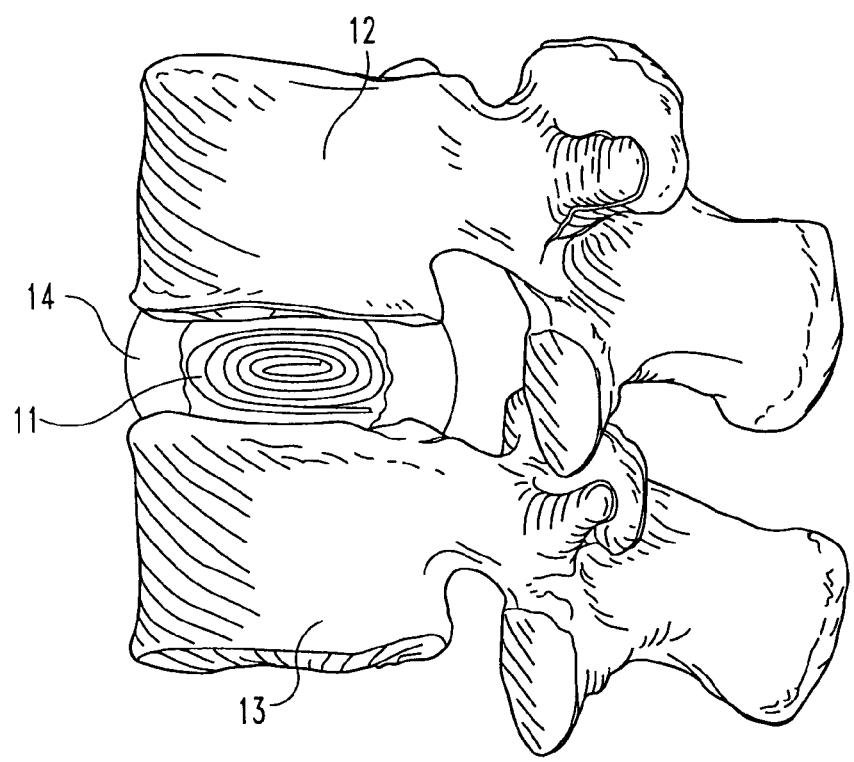
FIG. 1 is a side elevational view, in full section, of a roll of natural tissue material being used as a disc replacement device, according to one aspect of the present invention.

For the purpose of promoting an understanding of the principles of the invention, reference will now be made to preferred embodiments and specific language will be used to describe the same. It will nevertheless be understood that no limitation of the scope of the invention is thereby intended, such alterations and further modifications of the disclosed methods and/or devices, and such further applications of the principles of the invention as described herein, being contemplated as would normally occur to one skilled in the art to which the invention relates.

As briefly described above, one aspect of the present invention provides devices and methods for augmenting, repairing, or replacing all or part of an intervertebral disc using natural biological tissue. Natural, biological tissue is preferably used in the inventive devices and methods.

The tissue used in the present invention may be any natural biological tissue that is implantable in a human patient. In the most preferred embodiments the tissue will be selected from a tissue source appropriate to provide the strength and structural integrity necessary to function as described herein.

In some embodiments the tissue may be a flat tissue such as human, bovine, or porcine pericardium or small intestine submucosa (SIS). Ligaments such as anterior or posterior cruciate ligaments, fasciae such as fascia lata, tendons such as patella, hamstring, quadriceps and Achilles tendons, and other connective tissue may also be used.

The tissue may be autogenic, allogenic, or xenogenic with respect to the patient in which the tissue will be used. While human patients are particularly contemplated, animal patients may also be treated with the inventive devices and methods.

The tissue of the present invention is may be provided as one or more sheets, strips, plugs, fibers, or in any other form suitable for implantation. For example, when used to encapsulate a core to provide a disc or nucleus replacement device, the tissue has sufficient size and strength to at least partially constrain the core material. When used without an additional core material (for example, as a nucleus or disc replacement device itself), the tissue has sufficient size and strength to provide the desired structure. The size and strength of the implant varies, of course, according to whether it is used alone or in combination with other pieces, and with whether the tissue is used flat or is braided, folded, etc.

Consistent with the above, the natural tissue may vary in size and thickness depending on the configuration of the implant and how the material will be used. For example, when a sheet of tissue is to be rolled, folded or layered into a solid plug, the sheet will preferably be about 5-50 mm wide and about 20-80 mm long. In another example, when sheets or strips of tissue are to be used to encapsulate a core material, the sheets or strips will preferably be about 10-40 mm wide and about 30-60 mm long. When used to make a braided implant, strips that are about 30-200 mm long (more preferably about 50-100 mm long) by about 1-10 mm wide (more preferably about 2-5 mm wide) are often used. While thicker or thinner embodiments are occasionally preferred, in general the sheets will preferably be about 1-3 mm thick.

In one preferred embodiment the tissue is braided to form a braided implant. The braided implant may have superior strength when compared with unbraided implants, yet it may also provide sufficient flexibility to allow it to be bunched or folded to fill a disc space. In some preferred embodiments the braided implant is made from multiple (e.g., three or more) strips of flat tissue, while in other embodiments round strands are used. The braided implants may be braided to form extraordinarily strong, yet flexible, structures, such as when many thin/fine strands are braided together to form a natural tissue "rope." The rope may then be used as one long, thin section, or it may be folded or coiled to form a more bulky structure. As with the other embodiments described herein, the braided structures may be used in a variety of medical applications, including to augment, repair or replace all or part of an intervertebral disc, or to augment, repair or replace all or part of nearly any other anatomical structure, including ligaments, tendons, etc.

The natural tissue material may have elastic characteristics, or it may be inelastic. The tissue may also be deformable or non-deformable. For the purposes of this disclosure, elastic is understood to mean that the material returns to its original shape, or nearly so, when stretched or compressed under implant conditions. The elastic nature of the tissue provides the opportunity to better match the elastic modulus of surrounding host tissue, for example, thereby allowing the disc nucleus or disc replacement to flex more freely, to better contour to surrounding host tissues, and to reduce the potential for implant subsidence into the endplates. For purposes of this disclosure, deformable is understood to mean that the material may decrease slightly in dimension in response to surrounding forces once implanted into the defect site, such that it accommodates the site of injury's absent or deformed tissue within the body to enhance or restore function. Preferably, the natural tissue implants described herein are made of soft, flexible tissue, although hard, inflexible tissue may be used in some alternative embodiments.

The biological tissue may have smooth surfaces to reduce the potential for wear. Moreover, if wear particles are generated from the tissue material, the body can degrade and metabolize those particles better than it could degrade and metabolize synthetic materials.

It is to be appreciated that the use of natural, biological tissue provides the potential for "scarring" and allows host tissues to grow into the tissue, thus reducing the likelihood of expulsion of the implant as has been reported with synthetic jacket designs. In some embodiments the natural biologic material may be sutured before or after being positioned into place.

The tissue may comprise natural, biological tissue, or it may comprise a matrix derived from biological tissue. The biological tissue can be either degradable or non-degradable in nature. The tissue may be used to encapsulate an elastomeric or hydrogel nucleus or intervertebral disc replacement device, or it may be used as a nucleus or intervertebral disc replacement device itself, without an additional central core.

As to the inventive methods, the natural tissue material may be used to augment, repair, or replace all or part of an intervertebral disc, including a disc nucleus and/or a disc annulus, or it may be used to augment, repair, or replace all or part of some other orthopedic structure such as an anterior cruciate ligament, flexor tendon, rotator cuff, meniscus or other similar tissue within the body that may have elastic or deformable characteristics.

In one aspect, the natural material is to supplement or replace an intervertebral disc nucleus. In this aspect the natural tissue may be provided as a rolled, layered, braided, or folded "plug" of material (or series of such constructs) that are inserted into the disc annulus to supplement or replace the natural disc nuclear material. No synthetic core material is required in this aspect of the invention, but such a core could be incorporated if desired. The natural tissue implant may be used after a complete or partial discectomy with minimal, partial, or complete removal of the original disc nucleus.

In another aspect, the natural material may be used to supplement or replace all, or substantially all, of the original disc—including the disc annulus. Additionally this embodiment may include a retaining mechanism for holding the replacement disc in place, and could incorporate a synthetic core material if desired.

In a further aspect, the natural biological tissue may be used to encapsulate an elastomeric or hydrogel core to provide a nucleus replacement device. Hydrogel nucleus devices may require some form of encapsulation around the central hydrogel material to constrain them and make them compression resistant to loads across the disc. When natural tissue is used to encapsulate an elastomeric or hydrogel core, the advantages noted above are obtained.

In another aspect, the natural material may be used as a patch or plug to close a hole in the disc annulus, or otherwise to repair a disc nucleus or annulus. This and other aspects are described more fully in this and related applications, with reference to the drawings provided therein.

It is to be appreciated that the natural tissue implants of the present invention may be used in their hydrated form, or they may be fully or partially dehydrated prior to implantation. Dehydrated implant may be smaller than hydrated implants, and thus are preferred for some applications since they can be implanted through a smaller incision. In one embodiment a natural tissue implant is implanted into a disc space in a dehydrated condition, and is rehydrated to form a substantially larger body. In some such embodiments the rehydrated tissue increases in size enough to increase the disc height, and preferably enough to distract the vertebrae.

In some embodiments the natural tissue implants are used in combination with synthetic materials. In that regard, hydrogels may be used as indicated above, or other polymers, elastomers, plastics, fabrics, beads, fibers, etc., may additionally or alternatively be used. Examples of synthetic materials that may be used to form components of natural tissue implants include polyvinyl alcohol, polyacrylamide-polyacrylic acid, polyurethane, silicone, silicone polyurethane, polyethylene, propylene, polyester, polyterephthalate, polyaryletherketone, etc.

In some embodiments, growth factors such as TGF-Beta, BMP, etc. can be incorporated into the tissues to facilitate disc repair, regeneration or incorporation.

Referring to the Figures, FIG. 1 shows one embodiment of an intervertebral disc nucleus pulposus replacement device. In that Figure the natural tissue implant includes at least one piece of natural tissue 11 positioned between adjacent vertebra 12 and 13 and retained within annulus fibrosis 14. While the Figure illustrates the use of the implant to replace the entire disc nucleus, it is to be appreciated that the implant may be sized to replace or supplement all or only a portion of the actual nucleus pulposus, and to aid in maintaining a predetermined height of the disc space. Further, the illustrated implant has elastic characteristics to absorb forces transmitted through vertebrae 12 and 13. In this embodiment, for example, natural tissue 11 is configured as a roll of one or more sheets of tissue. Other suitable configurations may be utilized, however, as is discussed below.

Figure 2:
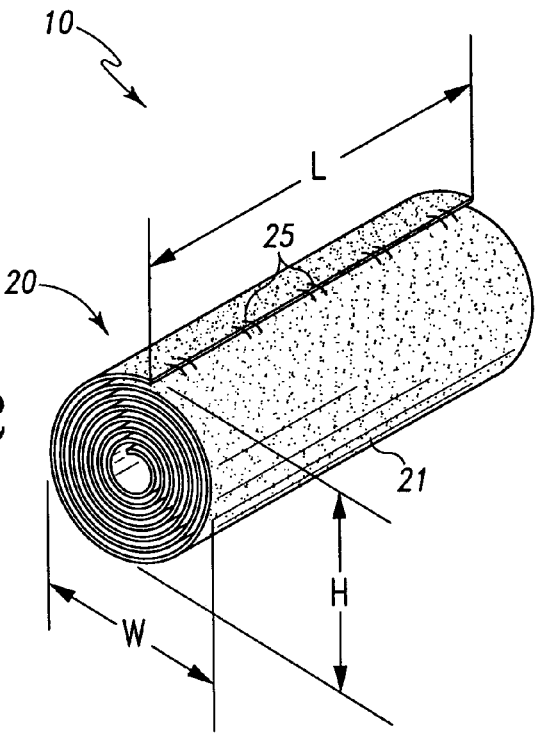
FIG. 2 shows a "roll" embodiment of the natural tissue implants of the present invention, according to one preferred embodiment.

Referring to FIG. 2, implant 20 in a state prior to implantation may have a greater height "H" and a smaller width "W" than the implanted device shown in FIG. 1 due to the lack of compressive forces on the implant. Further, implant 20 may include one or more securement mechanisms 25, such as sutures, staples and other fasteners as will be discussed below, for helping to maintain the given configuration of the implant. Securement mechanism 25 may extend along all or only a portion of the length of implant 10. Further, securement mechanism 25 may extend through all or only a portion of the thickness of implant 20.

Figure 3:
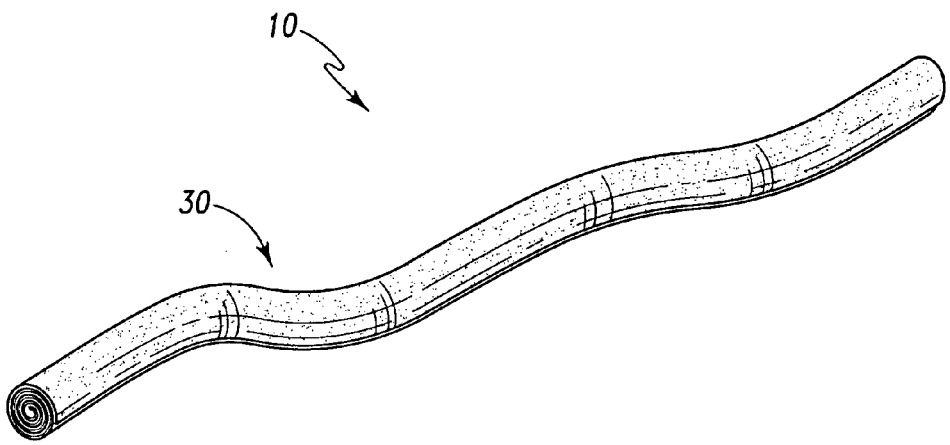
FIG. 3 shows an alternative embodiment of the roll of natural tissue shown in FIG. 2.

FIG. 3 shows an alternative embodiment of configurations of a natural tissue implant. In the illustrated embodiment, implant 30 comprises a long, thin roll of tissue that can be folded, coiled, etc. to fill a disc nucleus space.

Figure 4:
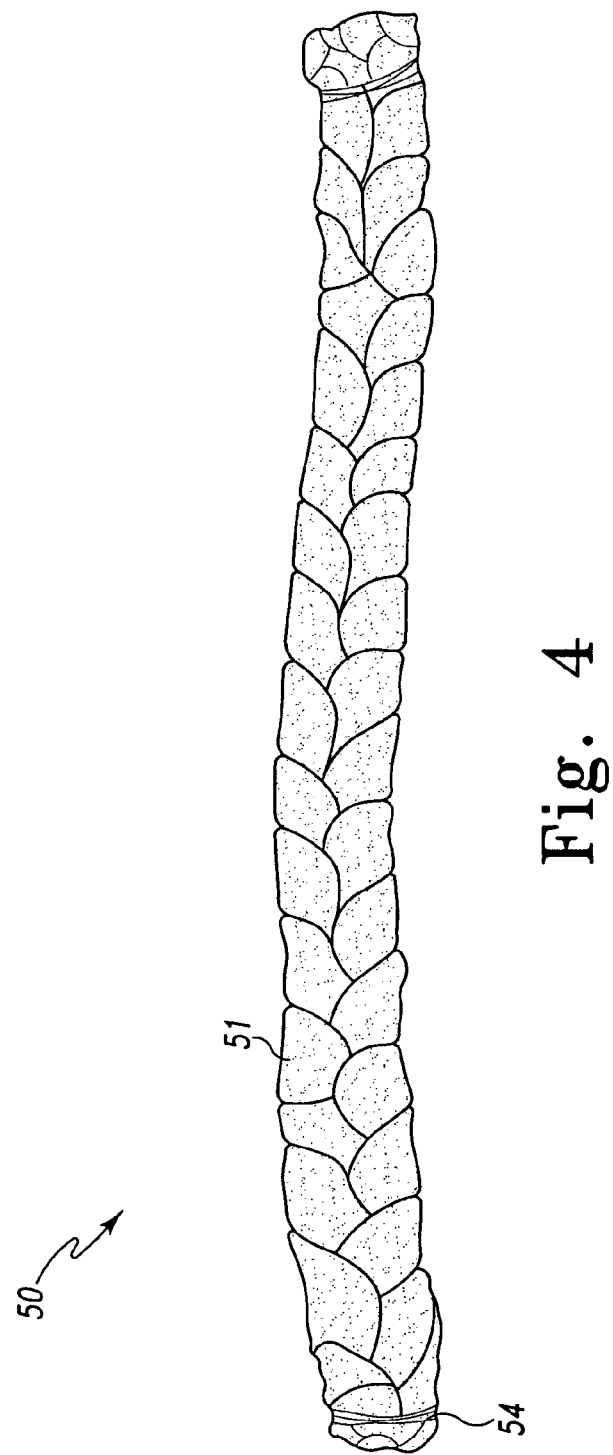
FIG. 4 shows a "braided" embodiment of the natural tissue implants of the present invention, according to one preferred embodiment.

FIGS. 4-10 show a "braided" embodiment of the natural tissue implant of the present invention. In FIGS. 4 and 5, implant 50 comprises long, braided strips 51 of natural tissue. A drawstring 52 is provided to assist in folding the implant into a more compact configuration after implantation. Drawstring 52 is secured to implant 50 near one end 54, passes through the implant at a multiplicity of sites throughout the length of the implant, and exits the other end 55 of the implant to provide a portion 53 for pulling the drawstring and bunching the implant. Preferably, drawstring 52 passes from one side of the implant to the other each time it passes through the implant. In this manner, the drawstring can be used to "bunch" or "fold" the implant up into a multiplicity of folded portions.

Implant 50 has a first, straightened configuration as shown in FIG. 4. In the illustrated embodiment, implant 50 has a length L that is at least five times its width W. More preferably, length L is at least ten times width W.

Figure 5A:
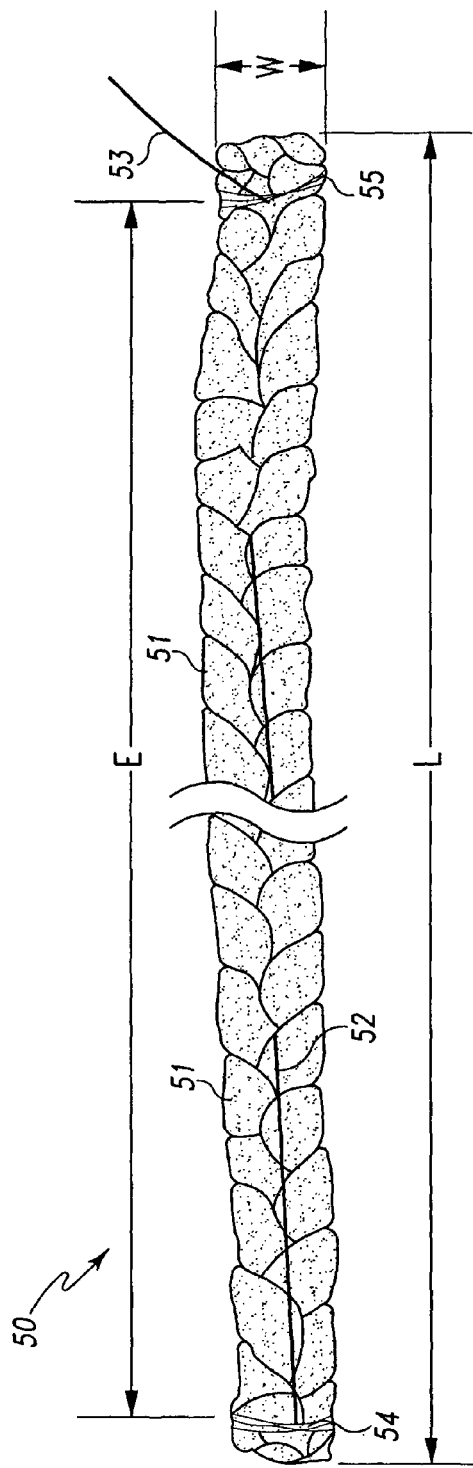
FIG. 5A shows a perspective view of the braided implant of FIG. 4, with a drawstring through the implant for causing the implant to bunch or fold.
Figure 5B:
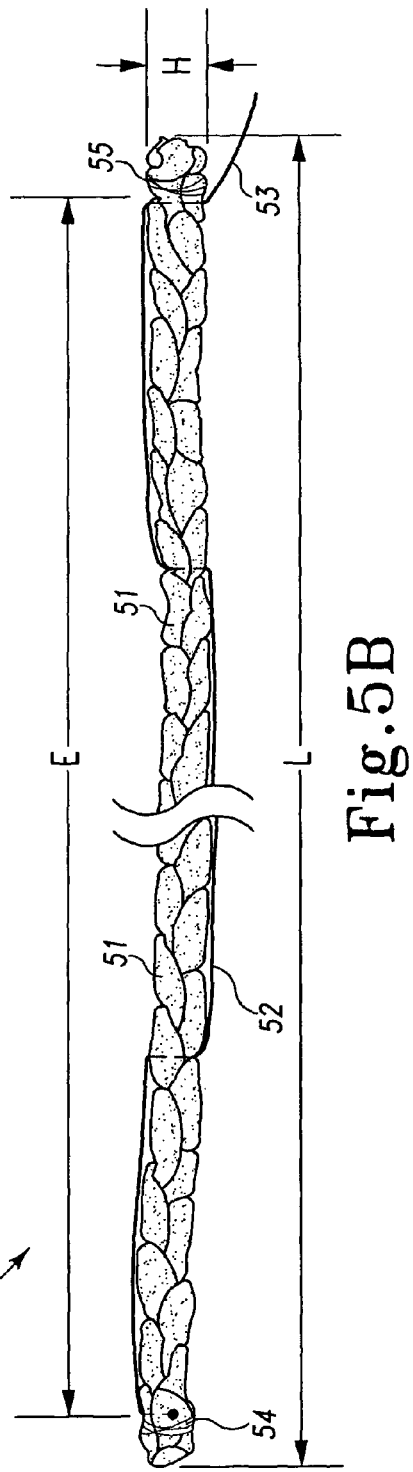
FIG. 5B shows another perspective view of the braided implant of FIG. 5A.

FIGS. 5A and 5B show the braided tissue implant of FIG. 4, with a drawstring passing through the implant. Drawstring 52 is secured near one end 54 of the braided tissue implant, and passes through the implant at a multiplicity of sites from the first, secured end, to the second, free end 55. As shown in FIG. 5B, drawstring 52 preferably passes from one side of the braided tissue implant to the other side of the braided tissue implant when it passes through the implant at the multiplicity of sites.

Drawstring 52 has an effective length "E" defined by the length of the drawstring from the point where it first enters the braid near one end, to the point where it last exits the braid near its other end. Drawstring 52 also includes an end portion 53 beyond its effective length, with end portion 53 being used to pull the drawstring and fold the braided implant. It is understood that for a specific length of drawstring, the relative portions of the drawstring that comprise the "effective length" and the "end portion" change as the drawstring is pulled to fold the implant.

To fold the implant, drawstring 52 is pulled while holding free end 55 in a generally fixed location. This causes secured end 54 of the implant to be drawn toward free end 55, thereby bunching or folding the implant. The number of folds depends on the number of sites in the implant through which drawstring 52 passes. For example, if drawstring 52 passes through implant 51 three times, three folds will be formed. The number of folds desired for a particular application varies, with at least one fold being preferred for some embodiments, at least two folds being preferred for other embodiments, and at least three folds being preferred for yet other embodiments.

Moreover, by providing a greater number of folds it may be possible to provide an implant having improved structural properties and/or a preferred volume. Also, by varying the length of the folds from implant to implant, or within a single implant, desired structural properties and/or a desired final configuration may be obtained. For example, wider folds may be obtained by passing the drawstring through the implant at sites that are farther apart, generally providing a wider, folded implant. Similarly, a curved or arc-shaped implant may be obtained by adjusting the location and size of the folds.

Figure 6:
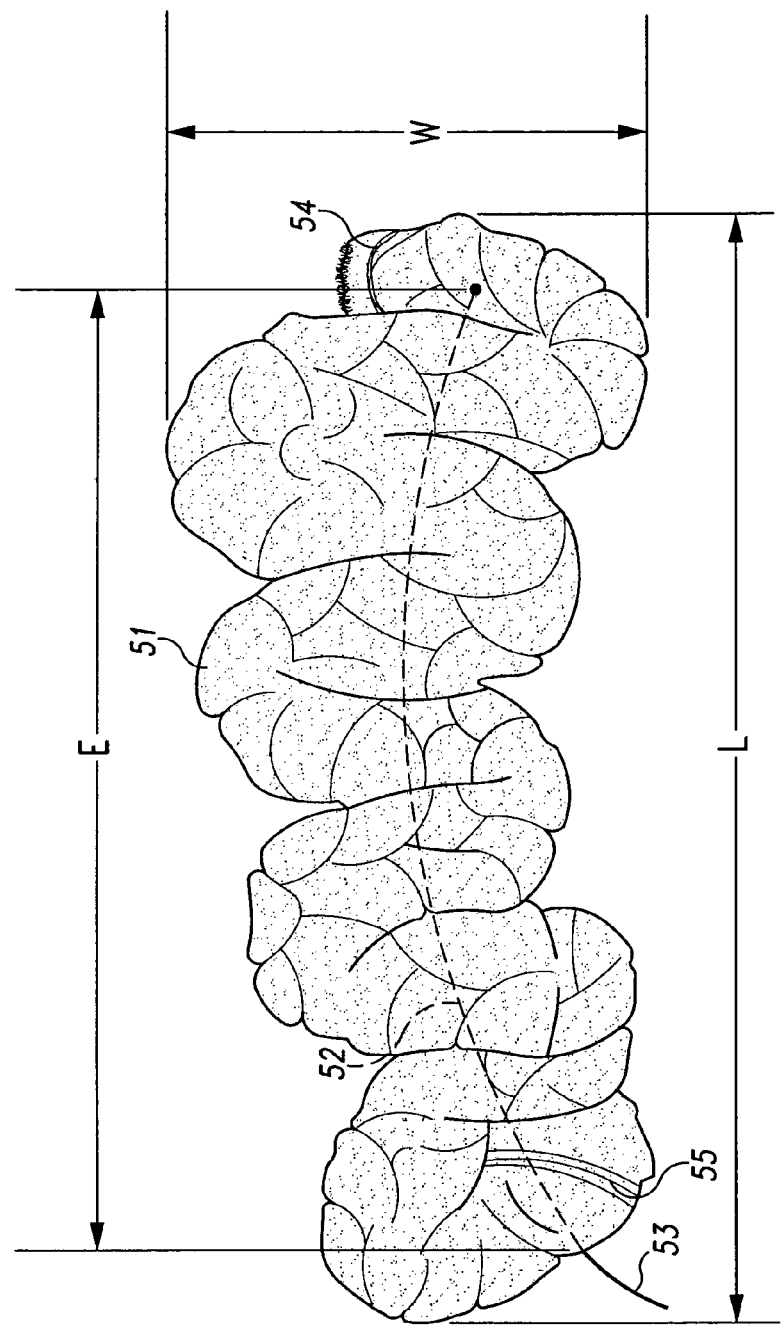
FIG. 6 shows the braided implant of FIG. 5 with the braid being folded after pulling the drawstring.

FIG. 6 shows implant 50 after the drawstring has been pulled and the implant has bunched or folded. The length L of the implant is reduced by the bunching/folding, while the width W is increased. Accordingly, in the illustrated embodiment implant 50 has assumed its second, folded configuration in which length L is less than five times width W. Preferably, in its folded configuration length L is no more than three times width W. The effective length of the drawstring has been correspondingly reduced, since less of the drawstring now lies adjacent to or within the braided tissue.

In some preferred embodiments, regardless of the original length and the original width of the straightened implant, the length-to-width ratio of the implant in its folded configuration is no more than one-half the length-to-width ratio of the implant in its straightened configuration. Accordingly, if the implant in its straightened configuration has a length-to-width ratio of 10:1, the length-to-width ratio of the folded implant is preferably no more than 5:1, although it is more preferably no more than about 3:1 as indicated above.

Figure 7:
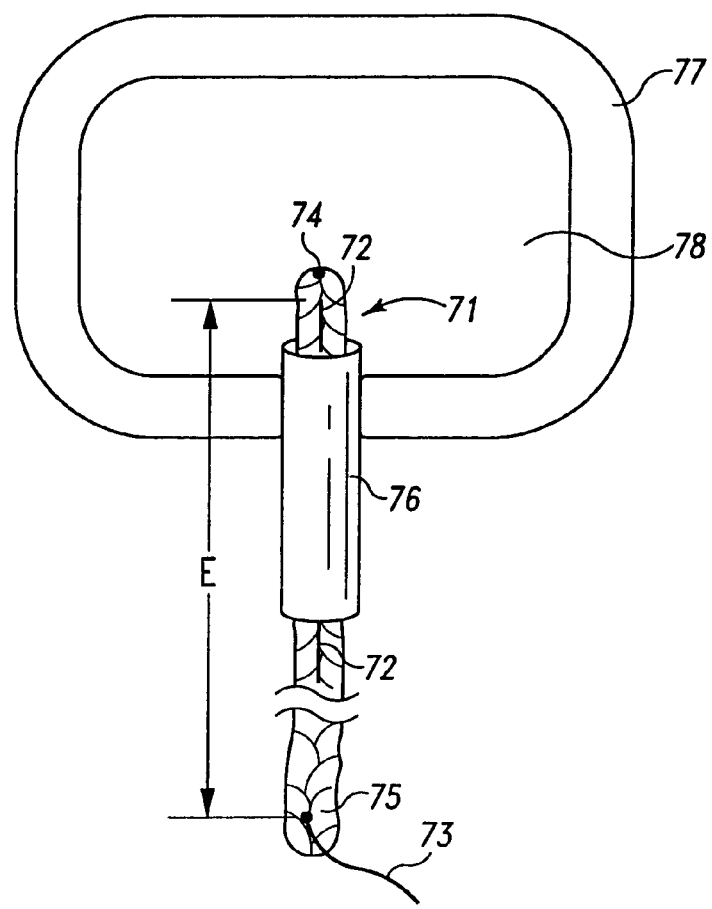
FIG. 7 shows the braided implant of FIG. 5 being implanted into a disc nucleus, with the implant in its first, straightened configuration.

FIG. 7 shows a braided implant being implanted into a disc nucleus space 78 defined by disc annulus 77. Implant 71 has a first end 74, a second end 75, and a length L that is at least five times its width W. A drawstring 72 is secured near first end 74, and passes through the implant and exits near second end 75. As previously described, drawstring 72 passes into and out of implant 71 at a multiplicity of sites throughout the length of the implant, and includes a free end portion 73. A cannula 76 may be used to assist in inserting the implant through the disc annulus.

Figure 8:
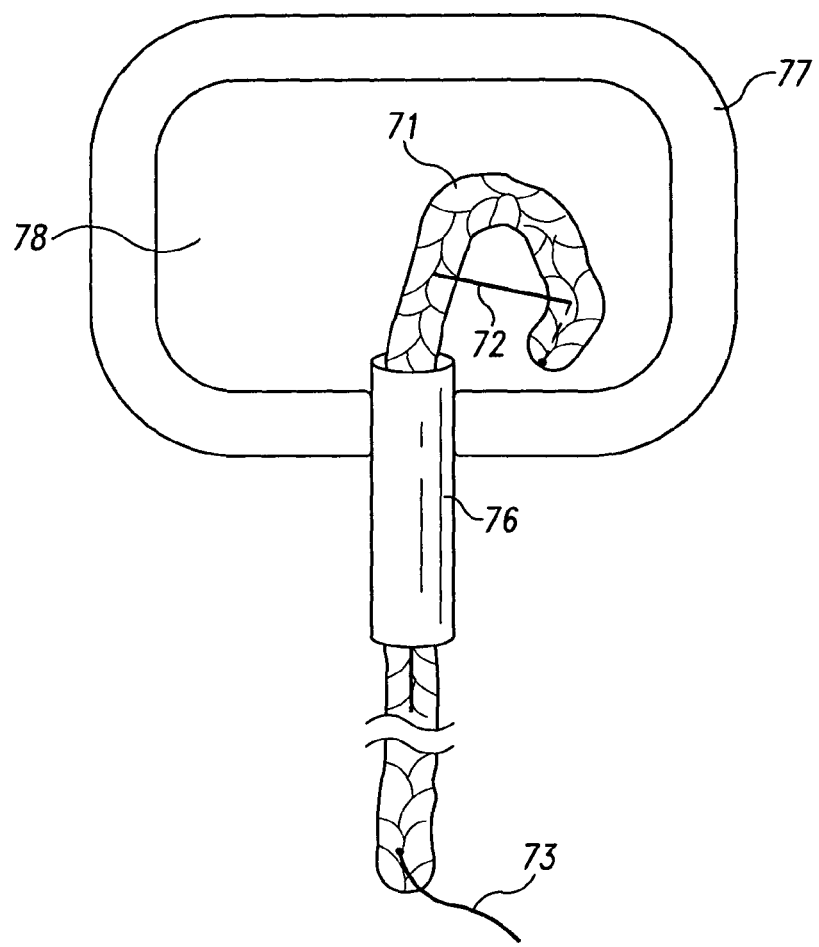
FIG. 8 shows the braided implant of FIG. 5 being implanted into a disc nucleus, with the implant beginning to fold.
Figure 9:
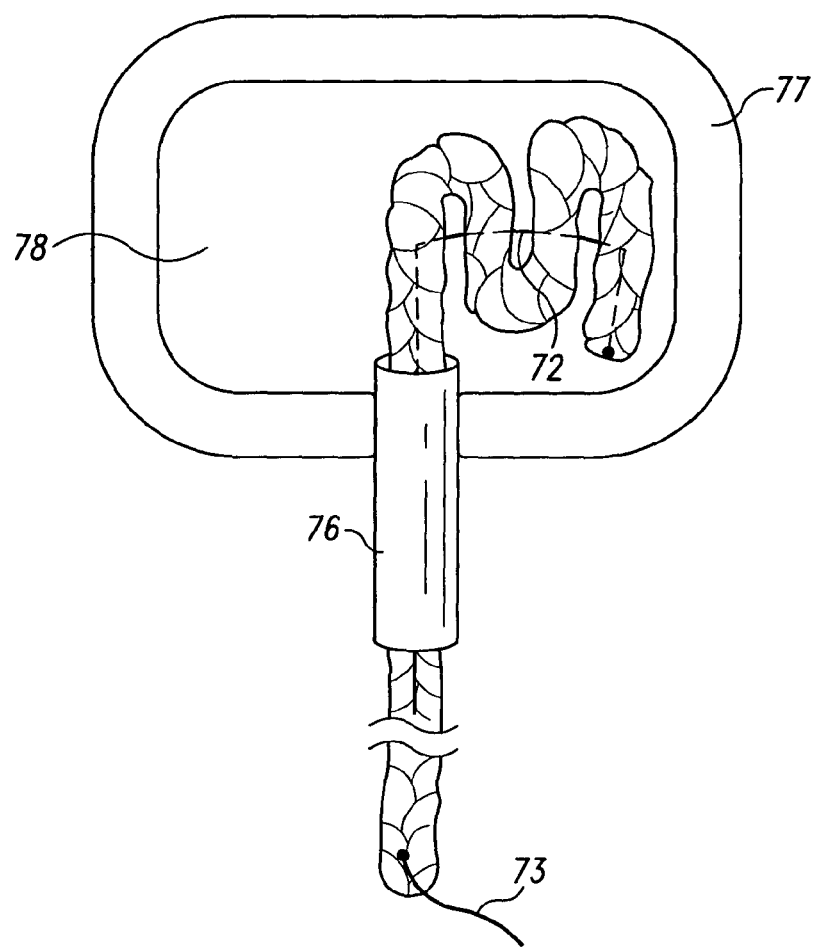
FIG. 9 shows the braided implant of FIG. 5 being implanted into a disc nucleus, with the implant continuing to fold.

FIG. 8 shows the implant of FIG. 7 after more of the implant has been implanted, and after drawstring 72 has been pulled somewhat to begin bunching/folding the implant in the disc nucleus space. FIG. 9 shows the implant after even more of the implant has been implanted, and after the bunching/folding has proceeded.

Figure 10:
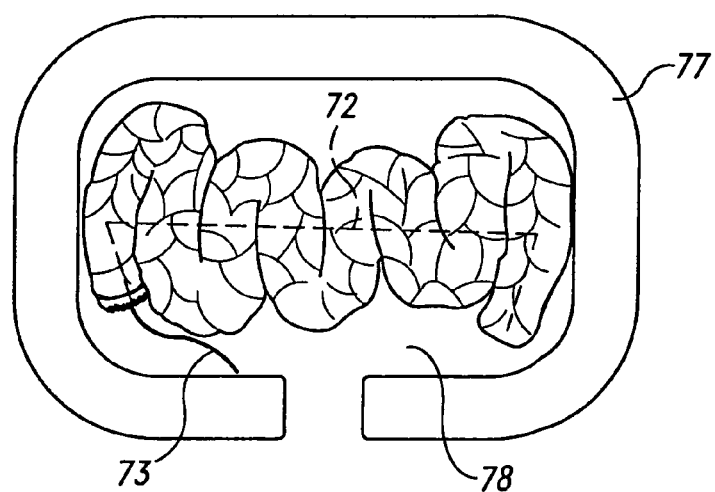
FIG. 10 shows the braided implant of FIG. 5 after it has been implanted into a disc nucleus, with the implant in its second, folded, or pleated, configuration.

FIG. 10 shows the implant of FIG. 7 after the implant has been implanted all of the way into disc nucleus space 75. Drawstring 72 has been pulled sufficiently to bunch or fold the implant completely so as to provide a pleated configuration, so that the width of the implant is now nearly as great as the length. As can been seen from the drawings, an implant having a length-to-width ratio of about 10:1 in its straightened configuration of FIG. 7, has been folded to an implant of pleated configuration having a length-to-width ratio of about 2.5:1 in its straightened configuration of FIG. 10.

Figure 11:
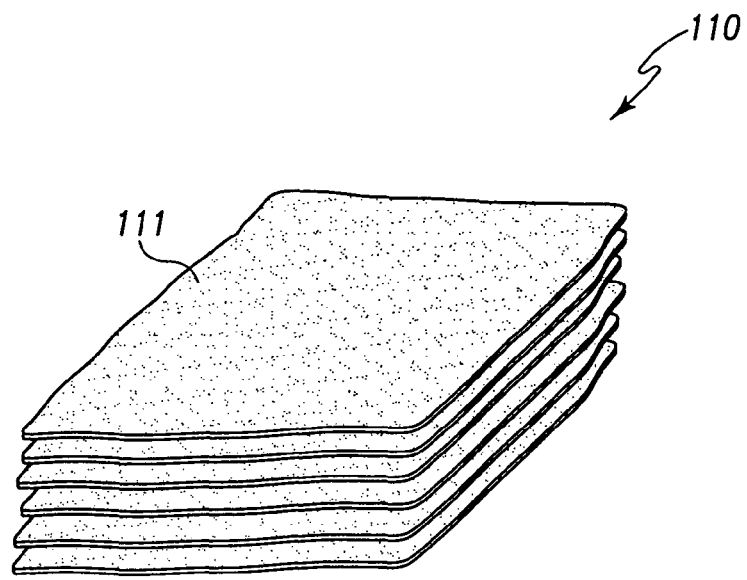
FIG. 11 shows a natural tissue implant made from a stack of separate sheets of tissue.
Figure 12:
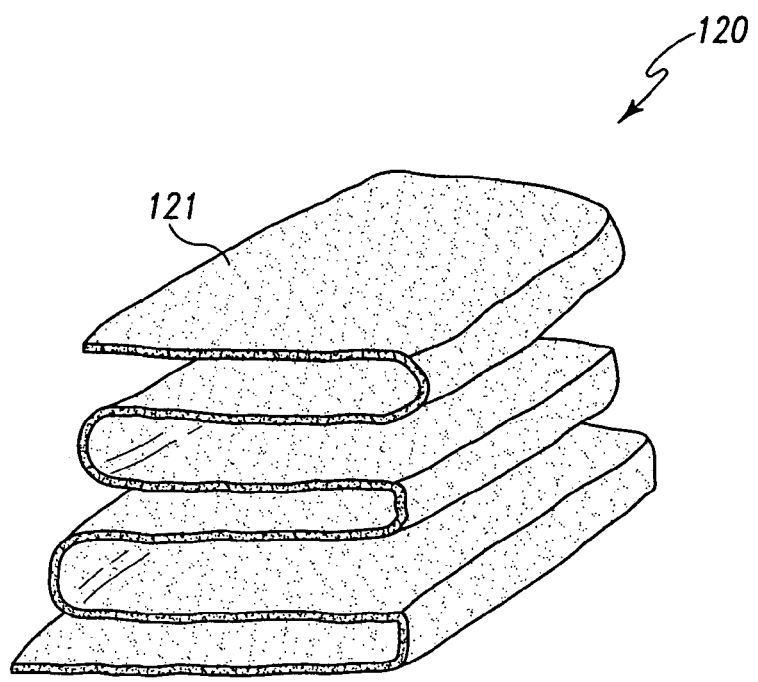
FIG. 12 shows a natural tissue implant made from a folded sheet of tissue.

As shown in FIG. 11, natural tissue implant 110 may comprise a stack of separate sheets 111. Alternatively, as shown in FIG. 12, implant 120 may comprise a strip 121 of tissue that has been folded over to form a multiplicity of layers in the implant. In all cases, stitches or sutures or another securement mechanism connecting one or more of the individual "layers" of material may be used to enhance construct integrity. Further, in all cases the implant may be cut or otherwise fashioned to form an implant having a more natural shape, such as the shape of a natural disc nucleus.

FIGS. 13-15 show another embodiment of a natural tissue implant 130. In FIG. 13, implant 130 comprise a plurality of sub-units 131, 132, 133, and 134, joined together by any appropriate securement means, such as sutures 135a-c. Most preferably, subunits 131-134 are relatively small (e.g., 5-9 mm in diameter and 8-20 mm in length) so that they can be inserted through a relatively small aperture in the disc annulus following a discectomy procedure, when stacked as shown in FIG. 13.

Upon implantation in a disc nucleus space, for example, sub-units 131-134 may be folded as shown in FIGS. 14 and 15 to form, in a second state, a substantially wider and shorter implant. Such an implant can, for example, better bear and distribute intervertebral forces.

It is to be appreciated that sub-units 131-134 need not be cynlindrical, and can be another shape, such as an ovid shape, where the height of the implant is greater than the width (e.g. 5-8 mm width, 8-10 mm height, and 8-20 mm length). This may facilitate creation of a smaller incision in the annulus to allow implantation. Moreover, a lesser or greater number of sub-units may be joined.

Figure 16:
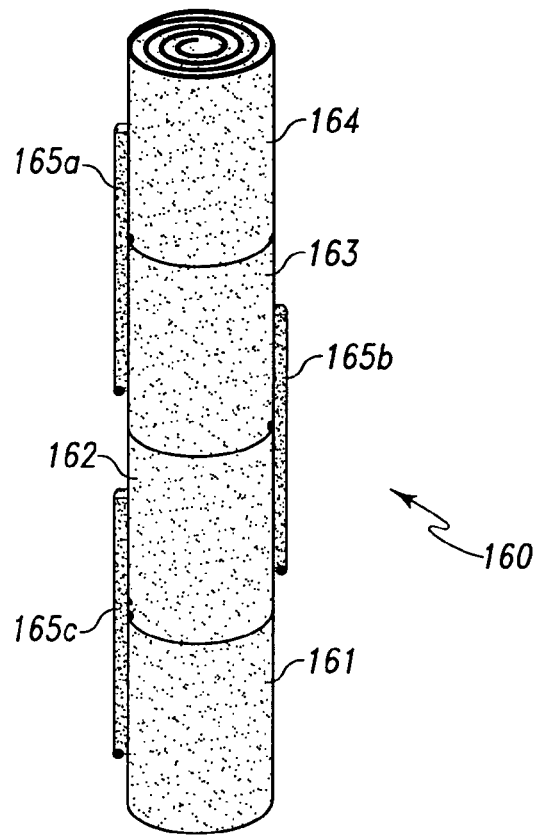
FIG. 16 shows an alternative embodiment of a natural tissue implant made from a multiplicity of sub-units, with each sub-unit comprising a roll of tissue.
Figure 17:
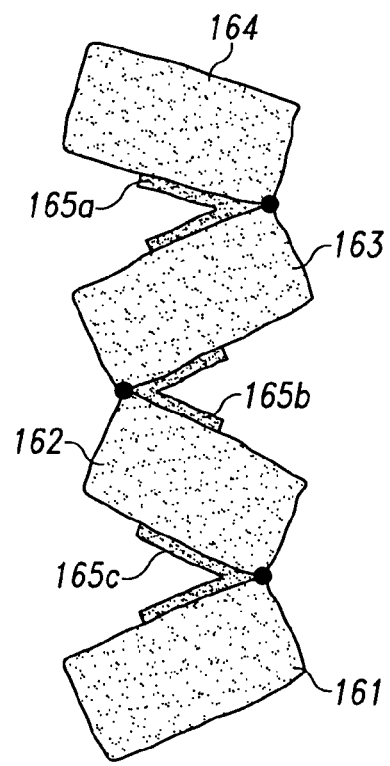
FIG. 17 shows the natural tissue implant of FIG. 16, with the sub-units being folded over to form a wider implant.

FIGS. 16-17 show an embodiment similar to that shown in FIGS. 13-15, but with implant 160 comprising a securement mechanism having sheets or strips of natural tissue 165a-c being attached to all or a portion of the sides of the sub-units 161-164 to act as hinges and facilitate folding.

Figure 20:
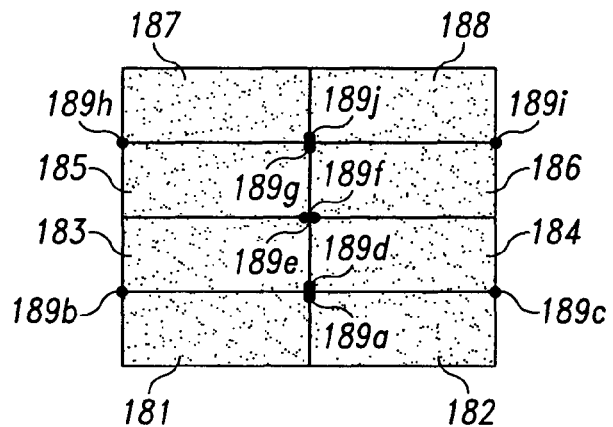
FIG. 20 shows the natural tissue implant of FIG. 18, with the sub-units folded to form a wider implant.

FIGS. 18-20 show a further embodiment of a disc nucleus replacement device, referred to hereinafter as an "accordion" embodiment. In those Figures, implant 180 comprises a multiplicity of sub-units 181-188, held together by securement means such as sutures 189a-j. As indicated by the Figures, implant 180 may assume a relatively long, narrow configuration in which the sub-units are folded in two columns of four subunits positioned end-to-end, or it may assume a relatively short, wide configuration in which the sub-units are folded in two columns of four sub-units positioned side-to-side. The long, narrow configuration may be used when the implant is contained in a syringe 190 or other implantation instrument, and the short, wide configuration may be used when the implant has been implanted in a disc space.

Figure 21:
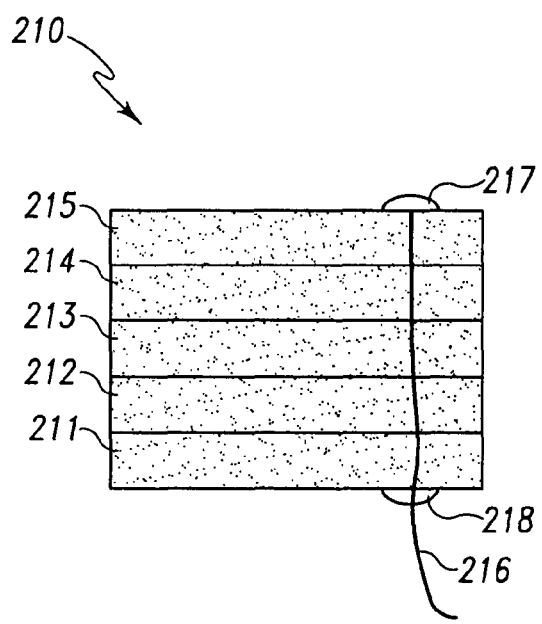
FIG. 21 shows a stack of natural tissue implants connected together with a suture.
Figure 22:
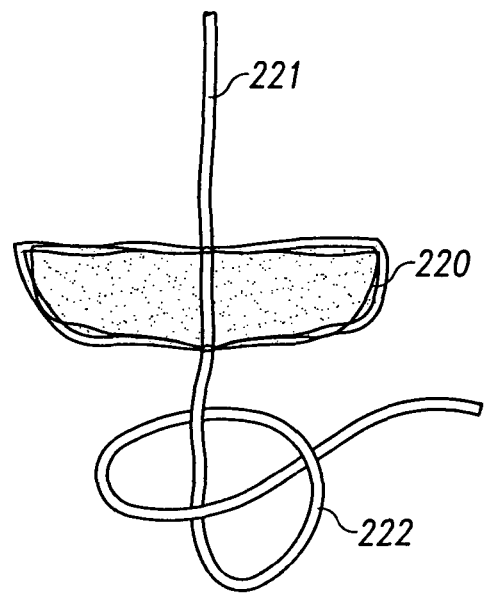
FIG. 22 shows a retaining clip for securing a stack of implants.
Figure 23:
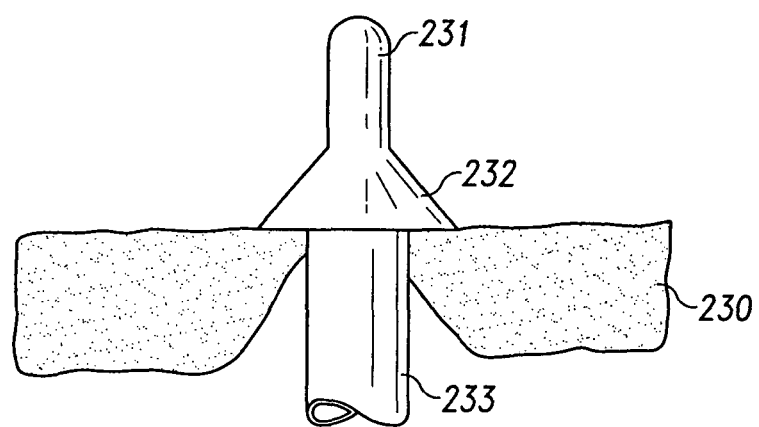
FIG. 23 shows an alternative retaining clip for securing a stack of implants.

It is also to be appreciated that a multiplicity of sub-units may be joined together with a long suture or cable 216, as shown in FIG. 21. Retaining clips 220 and/or 230 may be used as shown in FIGS. 22 and 23.

In another aspect, natural tissue is used as a constraining jacket to encapsulate a synthetic elastomeric or hydrogel core. The natural tissue allows the core material to flex and deform under disc loading conditions, while still providing the necessary structural support.

Figure 24:
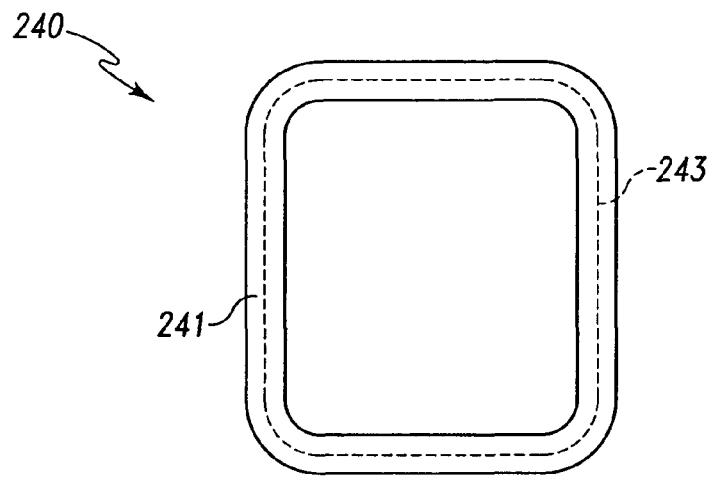
FIG. 24 shows a "pillow" embodiment of the natural tissue implant of the present invention.
Figure 25:
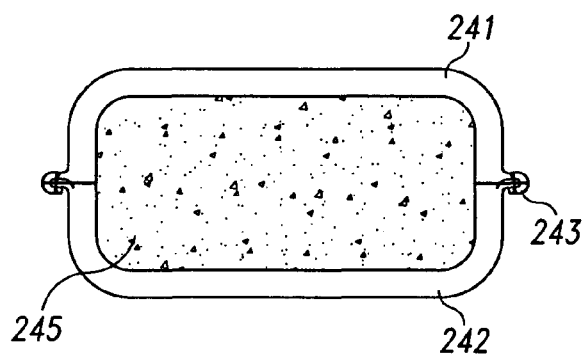
FIG. 25 shows a section view of the "pillow" embodiment of FIG. 24.

FIGS. 24 and 25 show one embodiment of the natural tissue of the present invention being used to encapsulate an elastomeric core. Natural tissue 241 constrains elastomeric core 245 to provide a disc nucleus or disc replacement device. Sutures 243 may be used to hold two pieces of natural tissue together to form the implant.

Figure 26:
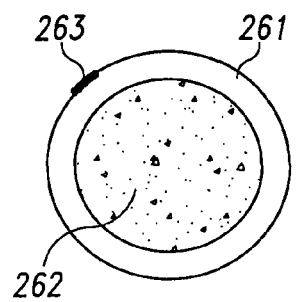
FIG. 26 shows an alternative "pillow" embodiment of the natural tissue implant of the present invention.

FIG. 26 shows another embodiment of the natural tissue of the present invention being used to encapsulate an elastomeric core. Natural tissue 261 constrains elastomeric core 262 to provide a disc nucleus or disc replacement device. Securement mechanisms such as sutures 263 are used to close the constraining jacket.

The disc nucleus or disc replacement device, with or without an additional core, may be used to replace part or all of a damaged disc nucleus. Further, when stabilized to prevent expulsion from the disc space, the disc replacement device may also replace part or all of the disc annulus. The use of a natural material to form the device provides the advantages identified above.

In another embodiment of the present invention the natural tissue is formed into a sack that is used to hold pieces of tissue. The sack and tissue contained therein may replace a natural disc nucleus.

Generally describing the "pouch" or "sack" embodiment, synthetic or natural tissue is fabricated into the shape of an empty pouch. This empty pouch can be compressed down to a diameter small enough to be inserted through a small hole in the annulus of an intervertebral disc. Once inside the disc it can be filled by inserting pieces, strips, or a long strand of natural or synthetic tissue into the pouch. This inflation is done through a small aperture in the pouch. Once filled to capacity the aperture in the pouch may be sutured closed with a purse string type suture or a preinserted suture in a flap over the aperture.

In yet a further embodiment the pouch and contents are manufactured out of material other than natural tissue, such as synthetic polymers (i.e. polyethylene, macron, etc.).

One advantage of the pouch embodiment is that it avoids the insertion of large implants through a large hole in the annulus. Because a large hole is not required to insert the prosthesis, the implants are less prone to expulsion from the disc. The pouch can also be inserted via a minimally invasive procedure.

Figure 27:
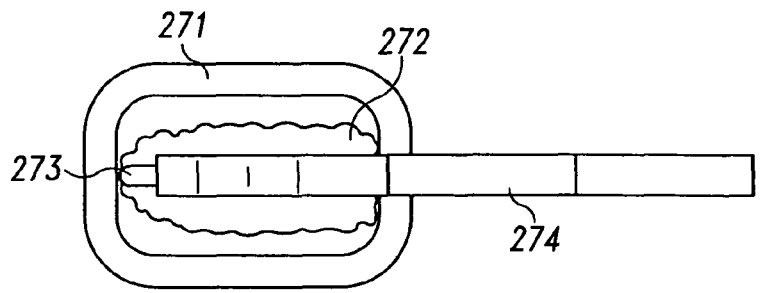
FIG. 27 shows a "pouch" embodiment of the present invention, with the pouch in the disc nucleus space and no tissue pieces in the pouch.
Figure 28:
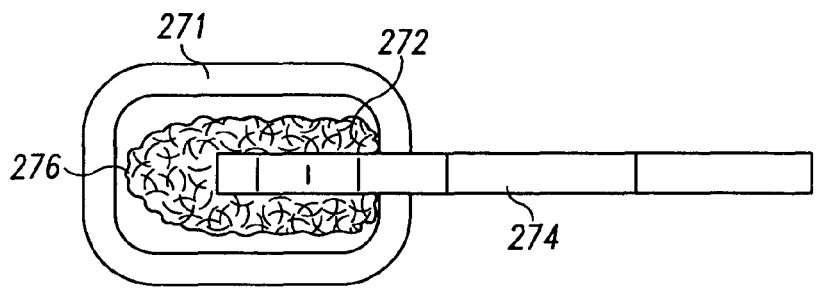
FIG. 28 shows the "pouch" embodiment of FIG. 27, with tissue pieces being inserted into the pouch.
Figure 29:
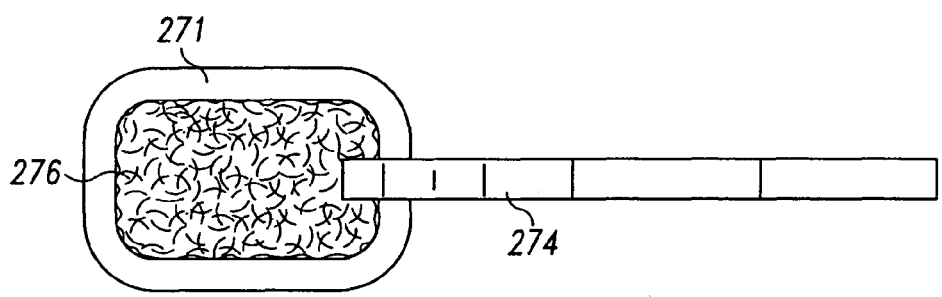
FIG. 29 shows the "pouch" embodiment of FIG. 27, with more tissue pieces being inserted into the pouch.
Figure 30:
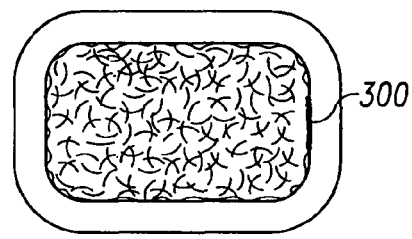
FIG. 30 shows the "pouch" embodiment of FIG. 27, after the tissue pieces have been inserted into the pouch and the pouch has been closed.

Referring to FIGS. 27-30, the pouch embodiment is shown. FIGS. 27-29 show a disc annulus 271 with a natural tissue pouch 272 inserted therein. A loading cannula having an insertion tool 273 may be used to insert pouch 272 into the disc space. To use the loading cannula, pouch 272 is preferably positioned over the loading cannula so that the cannula extends into the pouch. The insertion tool is used to push the pouch and cannula into position inside a disc annulus. The insertion tool is removed, leaving the cannula in place. After pouch 272 and cannula 274 are in place, the insertion tool 273 of the loading cannula is withdrawn, and pieces or strips of tissue 276 or synthetic material (not shown) are used to fill pouch 272 by passing them through cannula 274. The cannula is withdrawn part way as the pouch is filled to facilitate loading of the entire pouch. The cannula is withdrawn as the pouch is filed to a desired density. After the pouch has been filled, it is secured at the previously open end by a securement means such as sutures 300.

Figure 31:
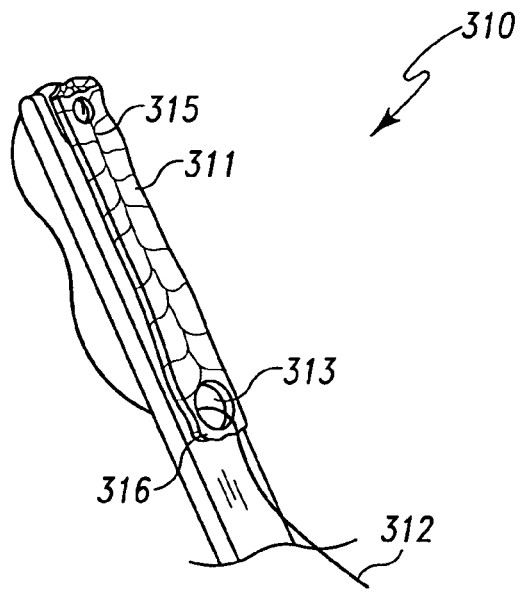
FIG. 31 shows and alternative embodiment of the present invention, with a braided tissue implant being formed into a knot.
Figure 32:
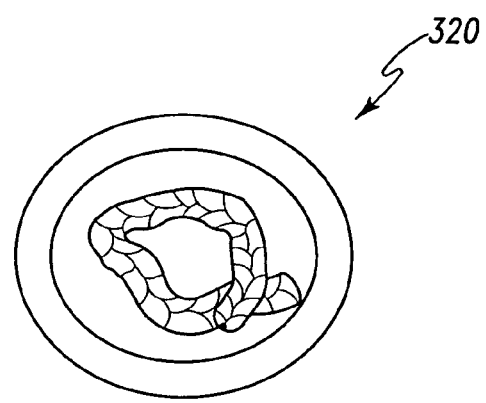
FIG. 32 shows the implant of FIG. 31, after the braided tissue implant has been formed into a knot.

In yet another embodiment, a natural tissue implant having a hole at one end is used with a drawstring to form a piece of folded tissue. As shown in FIG. 31, device 310 may comprise a natural tissue implant 311 having a first end 315, a second end 316, and a first hole 313. Using a drawstring 312 attached to implant 311 near end 315, the implant may be folded by pulling drawstring 312 through hole 313 to form a folded implant as shown in FIG. 32.

In another embodiment, implant 310 may be provided with multiple holes 313, and may be used as a ligament replacement by placing fixation screws through the holes.

A further embodiment is shown in FIGS. 33 and 34, with device 330 comprising a natural tissue implant 331 having a multiplicity of holes 333a-b. A drawstring 332 may be passed through holes 333a and 333b to fold the implant. In some embodiments, one end of the implant may be pulled through the to form a knotted implant, ad shown in FIG. 34.

FIG. 35 shows an embodiment similar to the braided embodiment of FIGS. 6-10, but with the implant comprising a strip or sheet of natural tissue that is not necessarily braided. Drawstring 352 is secured to one end 351b of tissue strip 351, and is used to fold the implant by pulling the free end of the drawstring while holding the free end 351a of implant 351 stable so that the remainder of the implant folds up. If desired, the drawstring may be passed through a loop 357 at one end of the drawstring to facilitate tying the drawstring in a knot to hold the folded implant in its second, folded configuration.

It is to be appreciated that alternative embodiments similar to the embodiment shown in FIG. 35 are contemplated, with all of those embodiments having the common feature of using a drawstring to bunch or fold a natural tissue implant. Accordingly, in those embodiments a body comprising natural tissue has a first, straightened configuration that is more narrow, and a second, folded configuration that is wider (when compared to the first, straightened configuration). This facilitates implanting the body through a small incision or hole, and folding the implant to a wider configuration after the body has been implanted.

It is also to be appreciated that the drawstring used to fold the natural tissue implants of the present invention may be made of natural tissue, or it may be made of another material. For example, synthetic materials may be used to form the drawstring. Such synthetic materials may be resorbable, or they may be non-resorbable. Alternatively, the drawstring may be made of wire or some other non-resorbable material. Moreover, multiple drawstrings may be used in a single device in some embodiments.

Reference will now be made to a specific example of one aspect of the present invention. It is to be understood that the example is provided to more completely describe one preferred embodiment, and that no limitation to the scope of the invention is intended thereby.

EXAMPLE

Figure 36:
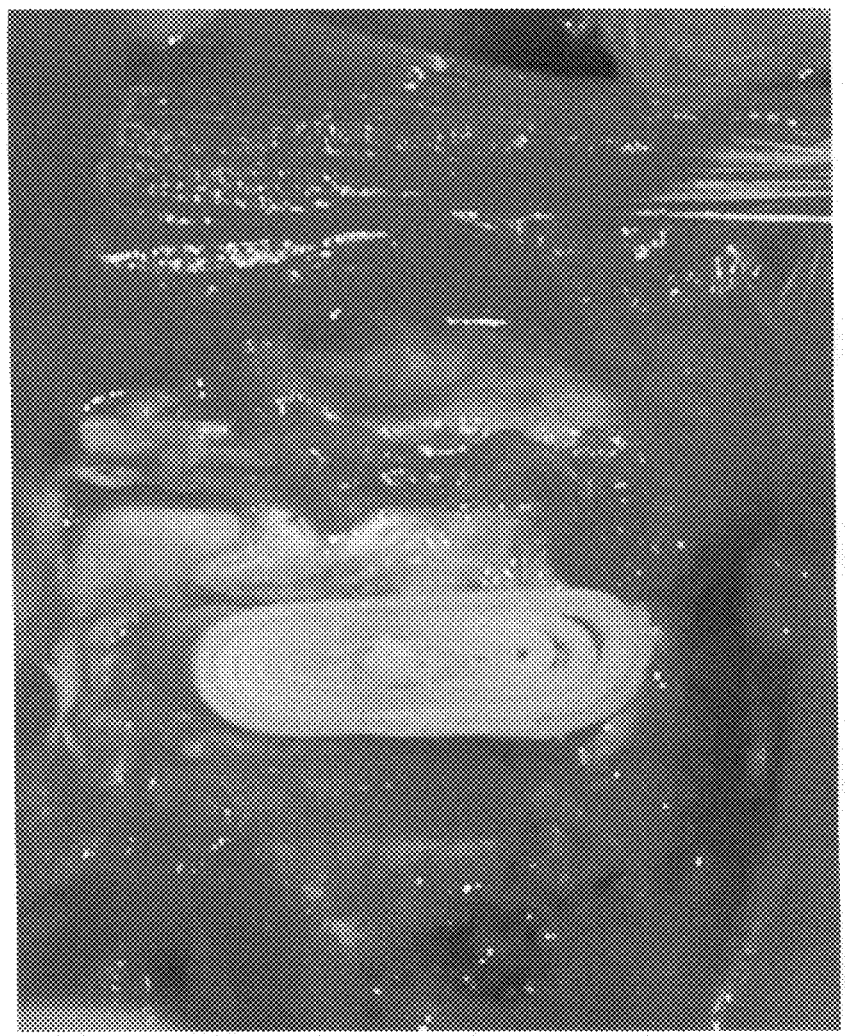
FIG. 36 is a photo of a roll of natural material being inserted for use as a disc replacement device, according to one aspect of the present invention.
Figure 37:
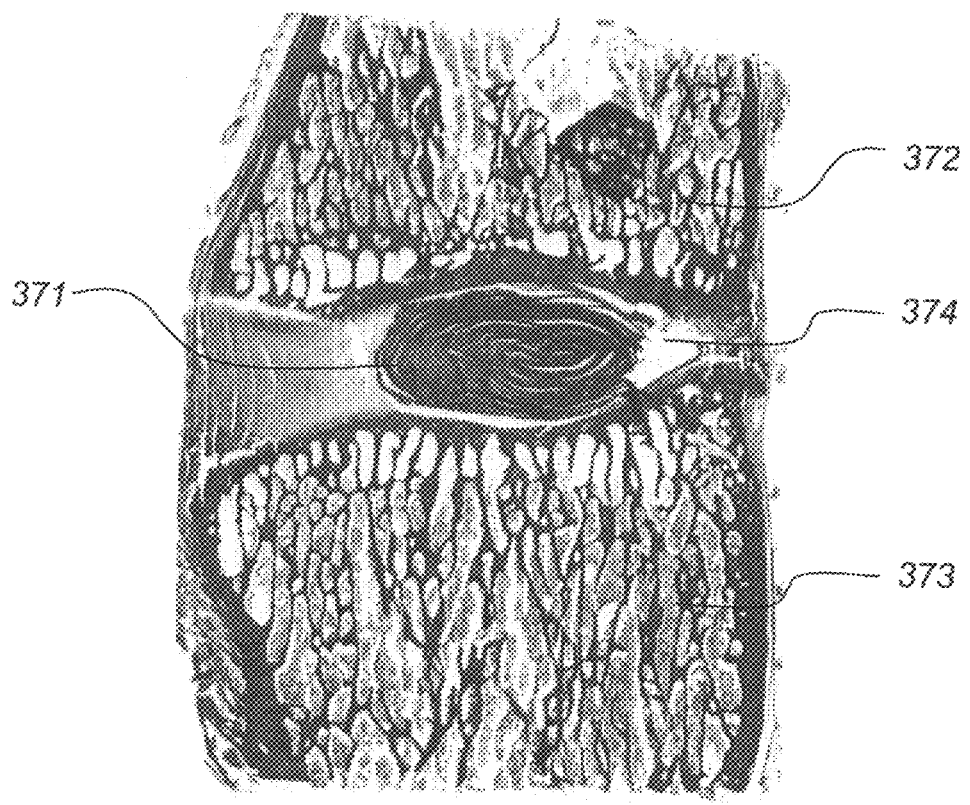
FIG. 37 is a histological section of a roll of natural material being used as a disc replacement device, according to one aspect of the present invention.

To test one aspect of the inventive device, a disc nucleus replacement device made of a roll of natural tissue was implanted in a sheep. A photo of the natural tissue device being implanted in the animal is shown in FIG. 36. A histological section showing the implant after six months in the animal is shown in FIG. 37. The disc nucleus replacement device functioned well for many months. The device remained in position within the nucleus space without expulsion, and maintained proper disc distraction and annulus tension without subsidence into the endplates. No evidence of wear particles, and no cellular inflammation were observed.

What is claimed is:

1. A method of augmenting the nucleus of an intervertebral disc, said method comprising the steps of:
    (a) implanting in the intervertebral disc an intervertebral disc device comprising a length of natural tissue sized for introduction into an intervertebral disc nucleus space and having a first end and a second end, wherein said length of natural tissue has a first, straightened configuration and a second, folded configuration having a multiplicity of pleated folds wherein said device additionally comprises a drawstring effective for folding said length of natural tissue to its second, folded configuration after implantation of the tissue in a disc nucleus space, said drawstring being secured to the length of natural tissue at or near the first end thereof, said drawstring passing through the tissue from one side thereof to another at a multiplicity of sites at predetermined intervals along the length of the tissue, exiting the tissue at or near the second end thereof and extending beyond said second end to terminate in an end portion for pulling the drawstring;
    (b) implanting at least a portion of said length of natural tissue starting with its first end into the disc nucleus space;
    (c) pulling the drawstring while holding the second end of the length of natural tissue stationary to cause the folding of the implanted tissue within the disc nucleus space; and,
    (d) repeating, if necessary, steps (b) and (c) until the full length of implanted natural tissue has acquired its second, folded configuration within the disc nucleus space.

2. The method of claim 1 wherein said natural tissue comprises a biological tissue or a matrix derived from a biological tissue.

3. The method of claim 1 wherein said natural tissue comprises pericardium tissue.

4. The method of claim 1 wherein said natural tissue comprises small intestine submucosa.

5. The method of claim 1 wherein said drawstring passes though the length of natural tissue at least three sites.

6. The method of claim 1 wherein said drawstring passes through the length of natural tissue at least five sites.

7. the method of claim 1 wherein said drawstring passes through the length of natural tissue at least 10 sites.

8. The method of claim 1 wherein the natural tissue is of braided construction.

9. The method of claim 1 wherein step (b) is carried out with the aid of a cannula.

* * * * *

UNITED STATES PATENT AND TRADEMARK OFFICE
CERTIFICATE OF CORRECTION

| | |
|---|---|
| PATENT NO. | : 7,887,593 B2 |
| APPLICATION NO. | : 10/666900 |
| DATED | : February 15, 2011 |
| INVENTOR(S) | : McKay et al. |

It is certified that error appears in the above-identified patent and that said Letters Patent is hereby corrected as shown below:

On the Face Page, in Field (73), under "Assignee", in Column 1, Line 1, delete "Inc." and insert -- Inc., Warsaw, IN (US) --, therefor.

In Column 1, Line 12, delete "Sep. 19, 2002," and insert -- Sep. 18, 2002, --, therefor.

In Column 9, Line 5, delete "75." and insert -- 78. --, therefor.

In Column 11, Line 17, delete "the to" and insert -- the hole to --, therefor.

In Column 12, Line 48, in Claim 5, delete "though" and insert -- through --, therefor.

In Column 12, Line 48, in Claim 5, delete "tissue at least" and insert -- tissue at at least --, therefor.

In Column 12, Line 50, in Claim 6, delete "tissue at least" and insert -- tissue at at least --, therefor.

In Column 12, Line 51, in Claim 7, delete "the method" and insert -- The method --, therefor.

In Column 12, Line 52, in Claim 7, delete "tissue at least" and insert -- tissue at at least --, therefor.

Signed and Sealed this
Twenty-sixth Day of April, 2011

David J. Kappos
*Director of the United States Patent and Trademark Office*